United States Patent

Nawa

Patent Number: 5,146,163
Date of Patent: Sep. 8, 1992

[54] METHOD AND APPARATUS HAVING TRANSVERSELY OFFSET EDDY CURRENT SENSORS FOR DETECTING DEFECT IN ELONGATED METAL STRIP JOINED BY WAY OF WELDING

[75] Inventor: Michio Nawa, Kanagawa, Japan

[73] Assignee: Kabushiki Kaisha Meidensha, Tokyo, Japan

[21] Appl. No.: 471,372

[22] Filed: Jan. 29, 1990

[30] Foreign Application Priority Data

Jan. 30, 1989 [JP] Japan ............................ 1-10310

[51] Int. Cl.⁵ .................. G01N 27/82; G01N 27/90; G01R 33/12
[52] U.S. Cl. ............................. 324/232; 324/237; 324/242; 340/676
[58] Field of Search ........ 324/222, 225, 227, 232–243; 340/675, 676; 73/159; 250/562, 563, 571, 572; 356/430, 431

[56] References Cited

U.S. PATENT DOCUMENTS

| | | |
|---|---|---|
| 2,746,012 | 5/1956 | Price ............................ 324/242 |
| 2,939,963 | 7/1960 | Rideout ........................ 250/562 |
| 3,141,952 | 7/1964 | Preston . |
| 3,247,453 | 4/1966 | Quittner . |
| 3,281,667 | 10/1966 | Dobbins et al. ............. 324/241 |
| 3,409,779 | 11/1968 | Fertig .......................... 250/562 |
| 3,437,918 | 4/1969 | Arnelo ......................... 324/238 |
| 3,469,182 | 9/1969 | Wycherley et al. ........ 324/242 X |
| 4,808,924 | 2/1989 | Cecco et al. ............... 324/242 X |

FOREIGN PATENT DOCUMENTS 2152218  7/1985  United Kingdom .

*Primary Examiner*—Gerard R. Strecker
*Attorney, Agent, or Firm*—Bachman & LaPointe

[57] ABSTRACT

An apparatus for detecting crack on an elongated metal strip employs a plurality of surface condition detecting means operating in synchronism with each other so as to detect the surface conditions of the orientations of the steel belt, which orientations are longitudinally the same position but transversely at different position. The apparatus further includes means for deriving a difference of outputs between the plurality of the surface condition detecting means. A discriminator means is also provided in the apparatus for discriminating the surface condition of the strip on the basis of the difference derived by the difference deriving means.

8 Claims, 2 Drawing Sheets

METHOD AND APPARATUS HAVING TRANSVERSELY OFFSET EDDY CURRENT SENSORS FOR DETECTING DEFECT IN ELONGATED METAL STRIP JOINED BY WAY OF WELDING

BACKGROUND OF THE INVENTION

1. Field of the Invention

The present invention relates generally to a method and apparatus for detecting defect or crack in an elongated metal strip, such as a steel belt. More specifically, the invention relates to a technology for discriminating defect or crack from intersection of two strips which are joined by way of welding.

2. Description of the Background Art

In apparatus employing an endless steel belt, such as a belt conveyer, a crack can be formed during operation of the apparatus. Once cracking occurs on the steel belt, breakage of the belt may subsequently occur to cause damage for associated components. Therefore, it is preferred to detect the occurrence of a crack in order to know the timing of maintenance of the steel belt. Conventionally, it is typical to monitor the condition of the steel belt by means of a non-contact type proximity switch. In the conventional technology, the proximity switch generates high frequency magnetic field to induce an eddy current on the steel. Magnitude of induced eddy current is variable depending upon the surface condition of the steel. Namely, when a crack is formed on the surface of the steel, magnitude of the induced eddy current fluctuates from that induced at the normal surface condition.

With such conventional crack detecting apparatus, a difficulty is encountered when the endless steel belt has a welded joining portion. Namely, the welded section has higher electric resistance than that in the general section of the steel belt. Therefore, the magnitude of induced eddy current at the welded portion becomes different from that of the normal surface. This brings erroneous judgement that the crack is caused on the steel belt.

SUMMARY OF THE INVENTION

Therefore, it is an object of the present invention to provide a method and apparatus for detecting a crack on the metal strip, which has capability of discriminating the welded portion from the crack.

In order to accomplish aforementioned and other objects, an apparatus for detecting cracks on an elongated metal strip, according to the present invention, employs a plurality of surface condition detecting means operating in synchronism with each other so as to detect the surface conditions of the orientations of the steel belt, which orientations are longitudinally the same position but transversely at different position. The apparatus further includes means for deriving a difference of outputs between the plurality of the surface condition detecting means. A discriminator means is also provided in the apparatus for discriminating the surface condition of the strip on the basis of the difference derived by the difference deriving means.

According to one aspect of the invention, a defect detecting apparatus comprises:

a first sensor placed within a path of an elongated metal strip for monitoring surface condition at a first transverse position of the elongated metal strip to produce a first sensor signal variable of signal level according to the variation of the surface condition at the first transverse position;

a second sensor placed within a path of the elongated metal strip for monitoring surface condition at a second transverse position of the elongated metal strip, which second transverse position is so oriented at an orientation transversely from said first transverse position of the elongated metal strip to produce a second sensor signal variable of signal level according to variation of the surface condition at the second transverse position;

third means for receiving the first and second sensor signals and deriving an error signal representative of a difference of the first and second sensor signals; and fourth means for comparing the error signal with a predetermined threshold value so that judgement that defect occurs in the elongated metal strip, is made when the error signal level is greater than the threshold value.

The elongated metal strip may be formed into an endless belt by adjoining both ends, and the adjoining portion of the endless belt extending substantially in transverse with respect to the axis of the path. Preferably, the first and second sensors may comprise proximity switches producing the first and second sensor signals variable of signal levels depending upon variation of resistance at the first and second transverse positions.

According to another aspect of the invention, a method for detecting a defect in an elongated strip being transferred through a predetermined path, comprises the steps of:

providing a first sensor within the path of an elongated metal strip for monitoring surface condition at a first transverse position of the elongated metal strip to produce a first sensor signal variable of signal level according to the variation of the surface condition at the first transverse position;

providing a second sensor within a path of the elongated metal strip for monitoring surface condition at a second transverse position of the elongated metal strip, which second transverse position is so oriented for monitoring transversely off-set position of the elongated metal strip to produce a second sensor signal variable of signal level according to variation of the surface condition at the second transverse position;

deriving an error signal representative of a difference of the first and second sensor signals; and comparing the error signal with a predetermined threshold value so that judgement that defect occurs in the elongated metal strip, is made when the error signal level is greater than the threshold value.

BRIEF DESCRIPTION OF THE DRAWINGS

The present invention will be understood more fully from the detailed description given herebelow and from the accompanying drawings of the preferred embodiment of the invention, which, however, should not be taken to limit the invention to the specific embodiment but are for explanation and understanding only.

In the drawings.

DESCRIPTION OF THE PREFERRED EMBODIMENT

Figure 1:
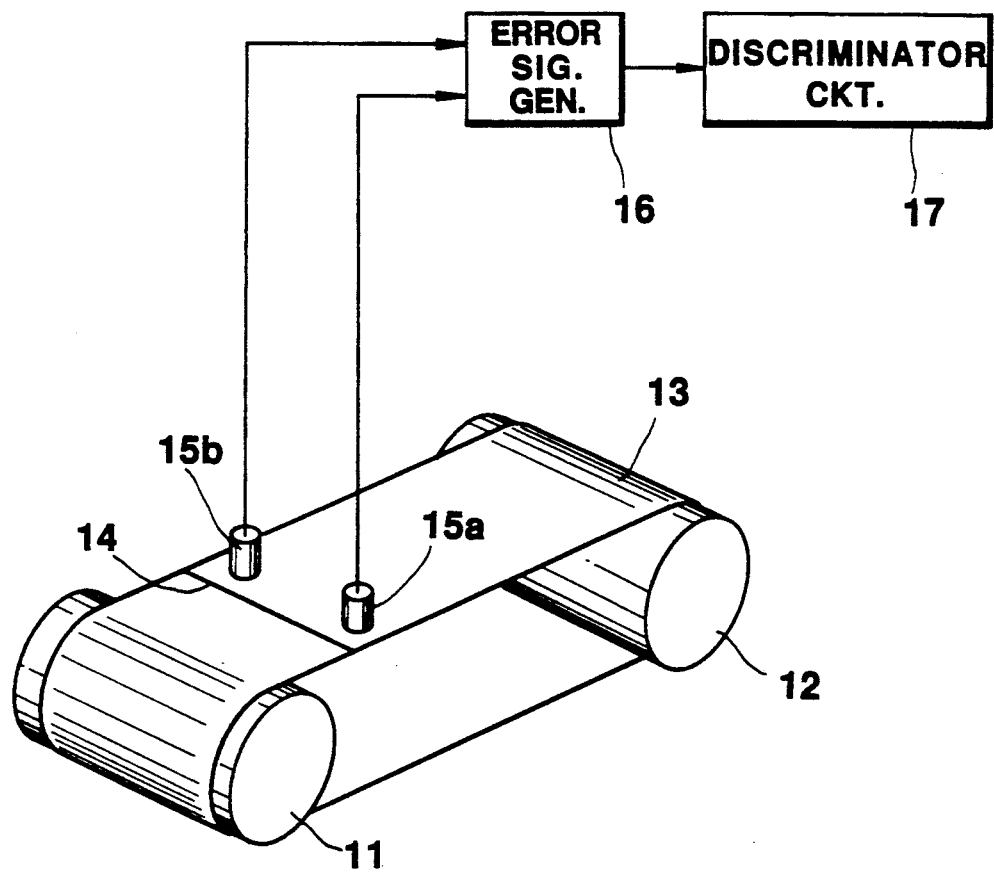
FIG. 1 is a perspective view of a belt drive apparatus employing an endless belt showing the preferred embodiment of a defect detecting apparatus according to the present invention.

Referring now to the drawings, particularly to FIG. 1, a belt drive apparatus, for which the preferred embodiment of the defect detecting apparatus according to the present invention, is applicable, comprises an endless metal belt 13 extending over a pair of rotary drums 11 and 12. The metal belt 13 may comprise an endless steel belt formed with a flexible steel strip with constant width by joining both ends together by way of welding. The welded joining portion 14 of the metal belt 13 extends generally in transverse with respect to the belt transferring axis. In order to drive the metal belt, one of the rotary drums 11 and 12 is connected to an electric motor or other driving power source (not shown) which provides rotational torque for the drum. The metal belt 13 is thus driven by the rotational torque applied from the driving power source via one of the rotary drums 11 and 12.

A pair of surface sensors 15a and 15b are provided in the vicinity of the belt path through which the metal belt is driven. The sensors 15a and 15b are arranged in transverse alignment with respect to the belt transferring axis and in spaced apart relationship with a predetermined distance to each other. Each of the sensors 15a and 15b comprises a proximity sensor which is per se of well known construction. As is well known, the proximity switch generates high frequency magnetic field for inducing eddy current on the metal belt surface and detects magnitude of current induced on the metal belt surface to produce a sensor signal representative of the detected induced current magnitude. Since the magnitude of the eddy current to be induced on the metal belt surface is variable depending upon the resistance, the signal values of the detector signals output from the sensors 15a and 15b vary according to variation of the resistance in the metal belt 13.

The sensors 15a and 15b are connected to an error signal generator 16. The error signal generator 16 receives the sensor signals from both of the sensors 15a and 15b to derive a difference of the signal values. The error signal generator 16 thus generates an error signal indicative of the derived difference. The error signal generator 16 outputs the error signal to a discriminator circuit 17. The discriminator circuit 17 checks the error signal level against a predetermined threshold level to make judgement that the crack occurs or not depending upon the error signal level.

Figure 2:
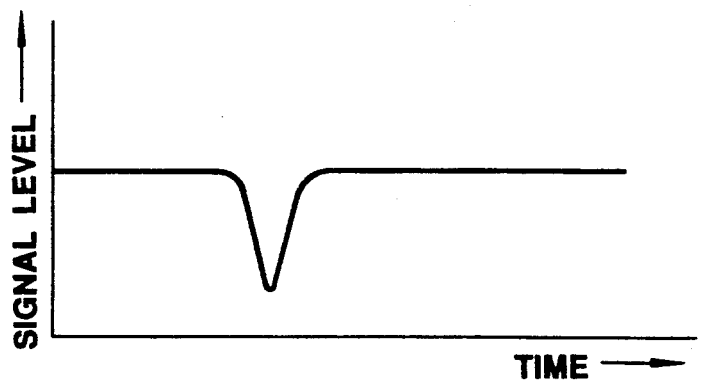
FIGS. 2 to 4 are chart showing variation of signal level of sensor employed in the preferred embodiment of the defect detecting apparatus of FIG. 1.

Here, assuming only the sensor 15a is used and the crack formed substantially in axial direction passes across the sensor, the signal level of the sensor signal produced by the sensor 15a varies as illustrated in FIG. 2. The similar waveform of FIG. 2 may appear when the welded joining portion of the metal belt 13 passes across the sensor 15a. Therefore, it makes discrimination of presence or absence of the crack difficult.

Figure 3:
Figure 4:
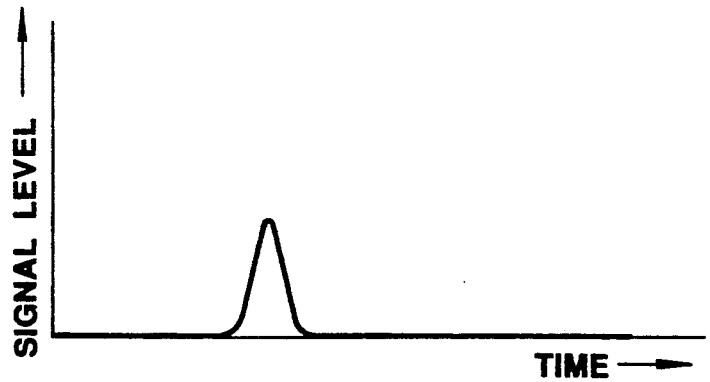

In the shown embodiment, the welded joining portion 14 can be detected simultaneously by the sensors 15a and 15b so that the essentially identical waveform appears on the sensor signal of the sensor 15b. Therefore, by obtaining the difference of the sensor signals of the sensors 15a and 15b, the signal level of the error signal at the welded joining portion is maintained substantially small, as shown in FIG. 3. On the other hand, when the local crack is created on the surface of the metal belt, the sensor signal level of the sensor 15a or 15b across which the crack containing portion of the belt travels, drops substantially. On the other hand, since the other sensor 15a or 15b does not detect the crack, the sensor signal level is maintained unchanged. In such case, the error signal level becomes substantial as shown in FIG. 4. Therefore, by utilizing a plurality of sensor and utilizing the difference of the sensor signals, the influence of the welded joining portion of the metal belt can be successfully avoided.

Figure 5:
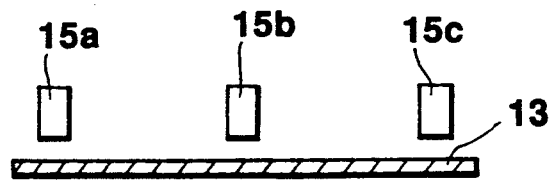
FIG. 5 is a section showing another embodiment of a defect detecting apparatus according to the invention.

FIG. 5 shows another embodiment of the defect detecting apparatus according to the present invention. In the shown embodiment, three sensors 15a, 15b and 15c are employed in spaced apart relationship with a predetermined distance and aligned transversely with respect to the axis of belt travel. In such case, two error signals are derived on the basis of the sensor signals of the sensors 15a and 15b and 15b and 15c. Based on the error signals thus derived, discrimination whether the defect, e.g. crack, is present or absent can be performed effectively and in more precise manner.

Therefore, according to the present invention, occurrence of crack can be successfully detected irrespective of the presence of the welded joining portion.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments and modifications to the shown embodiments which can be embodied without departing from the principle of the invention set out in the appended claims.

What is claimed is:

1. A defect or crack detecting apparatus for detecting a defect or crack in or on an endless belt form metal strip and for discriminating said defect or crack from a transverse welded portion having adjoining ends welded to each other, comprising:

a first sensor of a type which generates a predetermined high frequency magnetic flux toward a detecting region and detecting an eddy current generated in or on the detecting region and outputting a signal according to an electrical resistance of the eddy current generating region placed within a path of said endless belt form strip for monitoring whether said defect or crack is formed in or on a first transverse position of said endless belt form strip to produce a first sensor signal variable of signal level according to a result of monitoring whether said defect or crack is formed in or on said first transverse position of said endless belt form strip;

a second sensor electrically independent of said first sensor and of the same type as the first sensor, said second sensor being placed within a path of said endless belt form strip for monitoring whether said defect or crack is formed in or on a second transverse position of said endless belt form strip, which second transverse position is so oriented at an orientation transversely off-set from said first transverse position and at the same axial position to said first transverse position so that a presence or absence at the same transverse position can be monitored simultaneously with that of said first sensor to produce a second sensor signal variable of signal level according to a result of monitoring whether said defect or crack is formed in or on said second transverse position of said endless belt form strip;

an error signal generator for receiving said first and second sensor signals and deriving an error signal representative of a difference of said first and second sensory signals, said error signal having a substantially small signal level when said welded ends pass under said sensors and a larger signal level when said defect or crack passes under one of said sensors; and a discriminator circuit for comparing said error signal with a predetermined threshold value so that a judgement that a defect or crack occurs in said endless belt form strip is made when said error signal level is greater than said threshold value.

2. A defect or crack detecting apparatus as set forth in claim 1, wherein said metal strip in an elongated form is formed into an endless belt by adjoining both ends, and said adjoining portion of said endless belt extends substantially transverse to the axis of said path.

3. A defect detecting apparatus as set forth in claim 2, wherein said first and second sensors comprise proximity switches producing said first and second sensor signals variable of signal levels depending upon variation of resistance at said first and second transverse positions.

4. A method for detecting a defect or a crack in or on a metal elongated strip in a form of an endless belt loop with welded adjoining ends being transferred through a predetermined path, comprising the steps of:

providing a first sensor of a type which generates a predetermined high frequency magnetic flux toward a detecting region, detects an eddy current generated in or on the detecting region and outputs a signal according to an electrical resistance of the eddy current generated in or on the detecting region within said path of said elongated endless belt metal strip for monitoring whether said defect or crack is formed in or on a first transverse position of said elongated metal strip to produce a first sensor signal variable or signal level according to a result of monitoring whether said defect or crack is formed in or on said first transverse position of said endless belt metal strip;

providing a second sensor electrically independent of said first sensor and of the same type as the first sensor within a path of said elongated endless belt metal strip for monitoring whether said defect or crack is formed in or on a second transverse position of said elongated endless belt metal strip, which second transverse position is so oriented at an orientation transversely off-set from said first transverse position and at the same axial position to said first transverse position so that a presence of absence at the same transverse position can be monitored simultaneously with that of said first sensor to produce a second sensor signal variable of signal level according to a result of monitoring whether said defect or crack is formed in or on said second transverse position of said endless belt metal strip;

deriving an error signal representative of a difference of said first and second sensor signals, said error signal having a substantially small signal level when said welded ends pass under said sensors and a larger signal level when said defect or crack passes under one of said sensors; and 'comparing said error signal with a predetermined threshold value so that judgenent that said defect or crack occurs in said elongated metal strip is made when said error signal level is greater than said threshold value.

5. A method as set forth in claim 4, wherein said elongated metal strip is formed into an endless belt by adjoining both ends, and said adjoining portion of said endless belt extends substantially transverse with respect to the axis of said path.

6. A method as set forth in claim 4, wherein said first and second sensors comprise proximity switches producing said first and second sensor signals variable of signal levels depending upon variation of resistance at said first and second transverse positions.

7. A defect or crack detecting apparatus for detecting a defect or crack in or on an endless belt form metal strip having adjoining ends welded to each other, comprising:

a first sensor of a type which generates a predetermined high frequency magnetic flux toward a detecting region and which detects an eddy current generated in or on the detecting region and outputs a signal according to an electrical resistance of the eddy current generating region placed within a path of said endless belt form metal strip for monitoring whether said defect or crack is formed in or on a first transverse position of said endless belt form strip to produce a first sensor signal variable of signal level according to a result of monitoring whether said defect or crack is formed in or on said first transverse position of said endless belt form strip;

a second sensor electrically independent of said first sensor and of the same type as the first sensor, said second sensor being placed within a path of said endless belt form strip for monitoring whether said defect or crack is formed in or on a second transverse position which is oriented in transverse alignment with said first transverse position and transversely off-set from said first transverse position so that a presence or absence at said second transverse position can be monitored simultaneously with that of said first sensor to produce a second sensor signal variable or signal level according to a result of monitoring whether said defect or crack is formed in or on said second transverse position of said endless belt form strip;

third means for receiving said first and second sensor signals and deriving an error signal representative of a difference of said first and second sensor signals, said error signal having a substantially small signal level when said welded ends pass under said sensors and a larger signal when said defect or crack passes under only one of said sensors; and fourth means for comparing said error signal with a predetermined threshold value so that a judgement that defect or crack occurs in said endless belt form strip is made when said error signal level is greater than said threshold level.

8. A method for detecting a defect or crack in or on an elongated metal strip in a form of an endless loop with welded adjoining ends being transferred through a predetermined path, comprising the steps of:

providing a first sensor of a type which generates a predetermined high frequency magnetic flux toward a detecting region, detects an eddy current generated in or on the detecting region and outputs a signal according to an electrical resistance of the eddy current generated in or on the detecting region within said path of said elongated endless loop metal strip for monitoring whether said defect or crack is formed in or on a first transverse position of said elongated metal strip to produce a first sensor signal variable of signal level according to a result of monitoring whether said defect or crack is formed in or on said first transverse position of said endless loop metal strip;

providing a second sensor of the same type as the first sensor within a path of said elongated endless loop metal strip for monitoring whether said defect or crack is formed in or on a second transverse position of said elongated metal strip, which second transverse position is oriented in transverse alignment with said first transverse position and in transversely off-set position relative to said first transverse position so that a presence or absence at the same transverse position can be monitored simultaneously with that of said first sensor to produce a second sensor signal variable of signal level according to a result of monitoring whether said defect or crack is formed in or on said second transverse position of said endless loop metal strip;

deriving an error signal representative of a difference of said first and second sensor signals; and comparing said error signal with a predetermined threshold value so that judgement that said defect or crack occurs in said elongated metal strip is made when said error signal level is greater than said threshold value.

* * * * *